United States Patent [19]

Fedorov et al.

[11] Patent Number: 4,982,969
[45] Date of Patent: Jan. 8, 1991

[54] DEVICE FOR FIXING A DONOR'S EYEBALL

[76] Inventors: Svyatoslav N. Fedorov, ulitsa Dostoevskogo, 12, kv. 32; Leonid F. Linnik, ulitsa Deguninskaya, 17, kv. 36; Natalya I. Sukhareva, ulitsa 800-letia Moskvy, 5, korpus 3, kv. 127; Igor I. Korotkov, ulitsa Ierusalimskaya, 9, kv. 9, all of Moscow, U.S.S.R.

[21] Appl. No.: 278,835

[22] Filed: Dec. 1, 1988

[51] Int. Cl.$^5$ .............................................. A61F 9/00
[52] U.S. Cl. ..................................... 279/1 R; 269/130; 269/287
[58] Field of Search ............... 279/1 R; 269/130, 131, 269/132, 287; 606/107, 166; 248/176

[56] References Cited

U.S. PATENT DOCUMENTS 3,294,427  12/1966  Hunt ................................ 279/1 R

FOREIGN PATENT DOCUMENTS 1093412  5/1984  U.S.S.R. ............................ 279/1 R
1110553  8/1984  U.S.S.R. ............................ 279/1 R

Primary Examiner—Daniel W. Howell
Attorney, Agent, or Firm—Burgess, Ryan & Wayne

[57] ABSTRACT

The device for fixing a donor's eyeball comprises a body and retainers for holding the donor's eyeball to a support. The body is built up of an inner and an outer portions coaxially fitted one in the other with a possibility of rotating with respect to each other and of being held in a preset position. The retainers are made as a number of arcuate elements secured symmetrically with their one end on the inner body portion, and with the other end, on the outer body portion so as to interact with the donor's eyeball in a preset mutual arrangement of said body portions.

6 Claims, 2 Drawing Sheets

DEVICE FOR FIXING A DONOR'S EYEBALL

The invention relates to medical engineering and more specifically, to ophthalmology; it has particular reference to devices for fixing a donor's eyeball.

FIELD OF THE INVENTION

The invention can find application for training in microsurgery techniques on donor's eyeballs and for cutting out transplants in opthalmosurgical procedures.

BACKGROUND OF THE INVENTION

One state-of-the-art device for fixing a donor's eyeball (SU, A, 930,347) is known to comprise a body and retainers for fixing the donor's eyeball on a support, which is in fact a recess for the enucleated donor's eyeball. The retainers are in effect a set of rigid rings of different diameters and four spring-loaded tension braces.

For operation the eyeball is placed in the recess of the body, a ring is placed thereon and the eyeball is fixed with tension braces.

However, the rigid ring changes the natural eyeball shape and distorts the cornea, which tells adversely on the transplant and narrows the operative field, thus precluding one to manipulate on the sclera.

SUMMARY OF THE INVENTION

It is an object of the invention to preserve the shape of a donor's eyeball close to the natural one and to reliably fix the eyeball.

It is another object of the invention to provide higher accuracy and better convenience in cutting out a graft or transplant on a donor's eyeball.

It is one more object of the invention to extend the operative field and reduce postoperative complications.

And finally, the object of the invention is to provide an accurately measured intraocular pressure value with a possibility of its correction in the course of surgery.

Said objects are accomplished due to the fact that in a device for fixing a donor's eyeball, comprising a body and retainers for holding the donor's eyeball to a support, according to the invention, the body is built up of an inner portion and an outer portion, the former being fitted in the latter coaxially with a possibility of rotating with respect to each other and of being held in a preset position, while the retainers are made as a number of wire-like arcuate elements secured symmetrically with one of their ends on the inner portion of the body, and with their other ends, on the outer portion of the body so as to interact with the donor's eyeball in a preset mutual arrangement of said body portions.

It is preferred that the coaxially arranged inner and outer body portions be cylindrically shaped and have the respective ends of the wire-like arcuate elements secured thereto, said elements being held along a helical line having a helix angle of about 30 to about 45 degrees.

It is preferred that the wire-like arcuate elements be interlaced.

It is also preferred that the body accommodate a cylindrical insert having an off-centre recess.

It is preferred that the device be provided with a threaded plug fitted under the insert for adjusting the latter for height.

It is also preferred that one of the body portions be retained in position with respect to the other portion thereof with the aid of a ratchet mechanism accommodated in the body.

The fact that the body is of a sectionalized construction and the retainers are arc-shaped and attached in position in the aforesaid way provides for tight adherence of the retainers to the donor's eyeball, following its shape for retention of the natural shape of said eyeball and its reliable fixation.

When the respective ends of the arcuate elements are secured on the inner and outer body portions along a helical line having a helix angle less than 30 degrass, the donor's eyeball will be caught below its equator; when said angle exceeds 45 degrees the donor's eyeball will be distorted laterally.

The fact that the wire-like arcuate elements are interlaced renders them more strong and provides for their mutual bracing.

Provision of a cylindrical insert inside the body provides a seating surface for the donor's eyeball to rest upon.

Provision of a recess in the insert is necessary for placing the opthalmic nerve therein.

Provision of a threaded plug under the insert makes the latter adjustable for height for changing the intraocular pressure during surgery in the case of loss of the intraocular humor.

BRIEF DESCRIPTION OF THE DRAWINGS

Further objects and advantages of the present invention will become more obvious from a consideration of a detailed description of an exemplary embodiment thereof with reference to the occompanying drawings, wherein.

DETAILED DESCRIPTION OF THE INVENTION

Figure 1:
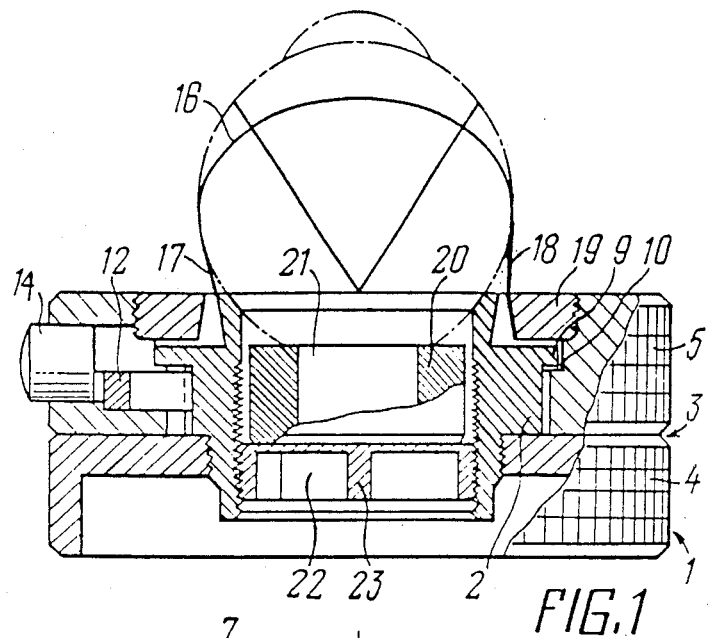
FIG. 1 is a schematic longitudinal sectional view of a device for fixing a donor's eyeball, according to the invention.
Figure 2:
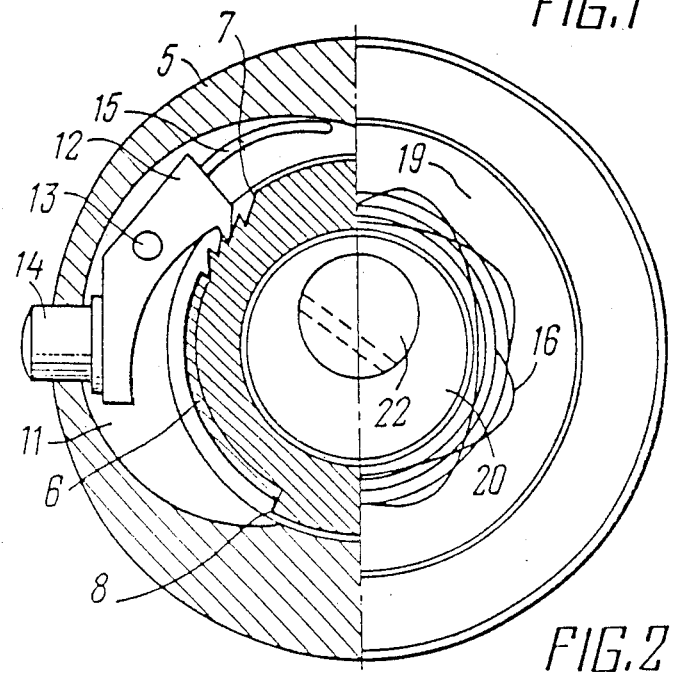
FIG. 2 is a plan view of the device of FIG. 1.
Figure 3:
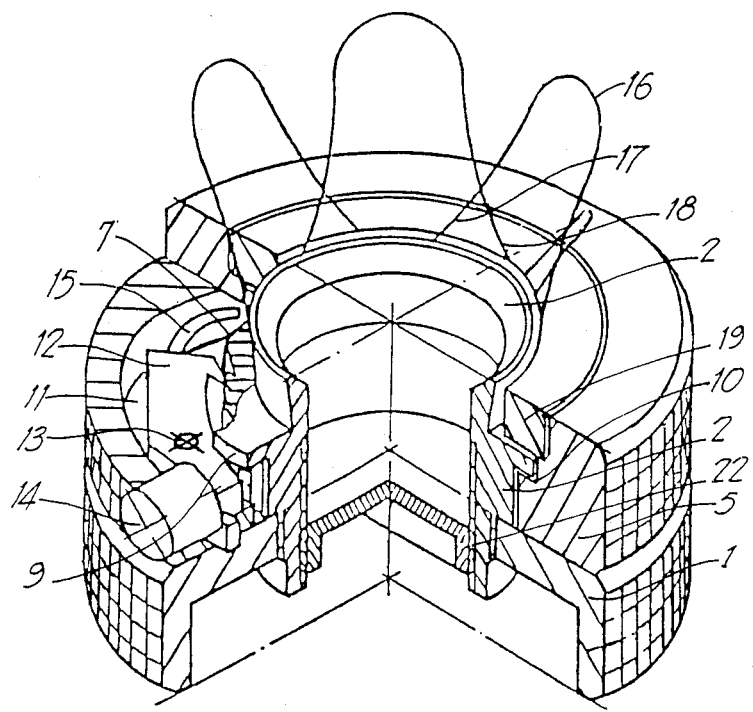
FIG. 3 is a cut-away perspective view of the device of FIG. 1.

The device for fixing a donor's eyeball comprises a body 1 (FIG. 1) built up of an inner portion 2 and an outer portion 3, the former being fitted coaxially in the latter with the ability to be rotated with respect to each other and of being held in a present position. The outer portion 3 is composed of a base 4 and a flange 5, both made of plastics. To hold the inner portion 2 and the outer portion 3 of the body 1 in a preset position the device has a known ratchet mechanism. The external surface of the inner portion 2 of the body 1 is shaped as the segment of a ratchet wheel 6 (FIG. 2) with stops 7, 8. A lip 9 is provided on the inner portion 2 (FIG. 1) of the body 1, adapted to interact with a recess 10 made in the flange 5. Situated below the recess 10 is a pocket 11 (FIG. 2) accommodating a pawl 12 (FIG. 2) of the ratchet mechanism, said pawl being adapted to interact with the segment of the ratchet wheel 6. A pivot 13 of the pawl 12 is held in position vertically with respect to the flange 5, and a knob 14 is provided on the side surface of the flange 5, adapted to retract the pawl 12 and a return spring 15 whose one end is held to the pawl 12 and the other end of said spring rests against the wall of the pocket 11. The device incorporates also a number of retainers shaped as four wire-like arcuate elements 16 (FIG. 1 and three) made fast symmetrically with one of their ends 17 on the inner portion 2 of the body 1, and with another end 18, on a washer 19 associated with the flange 5 of the outer portion 3 of the body 1 so as to interact with the donor's eyeball in a preset mutual arrangement of the inner portion 2 and the outer portion 3 of the body 1. The coaxially arranged inner portion 2 and outer portion 3 are cylindrically shaped and carry the respective ends 17, 18 of the arcuate elements 16, said ends being arranged along a helical line having a helix angle of from 30 to 45 degrees, said helix angle being equal to 45 degrees in the device discussed herein. In addition, the arcuate elements 16 are interlaced. A cylindrical insert 20 is accommodated in the inner portion 2 of the body 1, a through off-centre recess 21 being provided in said insert 20. The device has a threaded plug 22 fitted under the insert 20 for its adjustment for height. A bridge 23 is made in the threaded plug 22 for convenience in handling the threaded plug 22.

Operatin with the proposed device is carried out as follows.

The donor's eyeball is placed on the insert 20, with the occular nerve placed in the recess 21; the knob 14 of the retainer is depressed and the flange 5 is rotated clockwise, relative to the base 4. The ends 17 and 18 of the arcuate elements 16 move apart along an arc, causing the arcuate elements 16 to contact the eyeball and hold it fast. Depending on the donor's eyeball size or a required operative field, the insert 20 is either raised or lowered with the aid of the threaded plug 22. The surgery over, the knob 14 is depressed and the flange 5 of the outer portion 3 of the body 1 is turned all the way counterclockwise with respect to the inner portion 2 of the body 1 and the base 4 of the outer portion 3 so as to return the arcuate elements 16 to the initial position.

A total of twenty three surgeries have been performed for layer-by-layer and through keratoplasty without any postoperative complication. Besides, the device for fixing a donor's eyeball has been employed as a training facility for training ophthalmosurgeons in performing intra-and extracapsular cataract extraction, implanting an intraocular lens, keratotomy, reconstructive soleranguloplasty, perforating and non-perforating deep sclerectomy, layer-by-layer and through keratoplasty, and iridoplasty. The device provides for an accurately measured intraocular pressure value with a possibility of its correction in the course of surgery, which makes is possible to simulate a surgical procedure on a patient.

Use of the device for fixing 9 donor's eyeball enables one to attain higher accuracy of outting-out an opthalmic graft twofold, to extend the operative field from the limbus to the equator, and to make post-operative complications twice as less frequent.

What is claimed is:

1. A device for fixing a donor's eyeball, comprising:
   a body having an inner portion and an outer portion;
   the inner portion of said body fitted coaxially in the outer portion of said body, rotatable with respect to said outer portion and having means to retain the inner portion in a present position in relation to the outer portion;
   retainers comprising a number of arcuate elements, secured symmetrically with one of their ends on said inner portion of said body, and with the other end secured on said outer portion of said body whereby upon relative rotation of the outer portion in relation to the inner portion, the ends of the arcuate elements are moved apart so that the arcuate elements interact with the donor's eyeball.

2. A device as claimed in claim 1, wherein said coaxially arranged inner and outer portions of said body are cylindrically shaped and have secured thereon the respective ends of said arcuate elements, said ends being secured along a helical line whose helix angle ranges between about 30 and about 45 degrees.

3. A device as claimed in claim 1 or 2, wherein said arcuate elements are interlaced.

4. A device as claimed in claim 1 or 2, wherein a cylindrical insert is accommodated in said body, an off-center recess being made in said insert to accept an optic nerve of said eyeball.

5. A device as claimed in claim 4, wherein a threaded plug fitted under said insert is provided for adjusting a vertical position of said cylindrical insert.

6. A device as claimed in claim 1 or 2, wherein a ratchet mechanism is provided for holding the inner and outer portions of said body in said preset position.

* * * * *